United States Patent [19]

Suyama et al.

[11] Patent Number: 5,012,010
[45] Date of Patent: Apr. 30, 1991

[54] T-ETHYL-1,5-DIMETHYLHEXYLPEROXY ACID ESTERS

[75] Inventors: Shuji Suyama; Tomoyuki Nakamura, both of Chita, Japan

[73] Assignee: Nippon Oil and Fats Company, Limited, Tokyo, Japan

[21] Appl. No.: 407,107

[22] Filed: Sep. 14, 1989

[30] Foreign Application Priority Data

Sep. 20, 1988 [JP] Japan .................................. 63-233395
Oct. 12, 1988 [JP] Japan .................................. 63-254773
Dec. 9, 1988 [JP] Japan .................................. 63-310186

[51] Int. Cl.$^5$ ............................................ C07C 409/00
[52] U.S. Cl. .................................... 568/561; 568/563; 568/566
[58] Field of Search .................. 568/563, 561, 566

[56] References Cited

FOREIGN PATENT DOCUMENTS

| 40-16795 | 7/1965 | Japan | 568/563 |
| 51-38752 | 10/1976 | Japan | 568/563 |
| 52-76353 | 6/1977 | Japan | 568/563 |
| 54-3847 | 2/1979 | Japan | 568/563 |
| 58-120611 | 7/1983 | Japan | 568/563 |
| 58-120613 | 7/1983 | Japan | 568/563 |
| 62-30064 | 6/1987 | Japan | 568/563 |

Primary Examiner—Mary C. Lee
Assistant Examiner—Robert C. Whittenbaugh
Attorney, Agent, or Firm—Stevens, Davis, Miller & Mosher

[57] ABSTRACT

A novel peracid ester represented by the general formula (I):

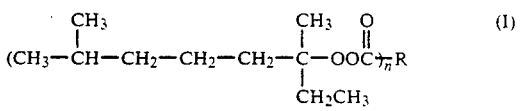

is useful as a polymerization initiator for vinyl chloride monomer, a curing agent for unsaturated polyester resin or a crosslinking agent for polymers.

2 Claims, No Drawings

T-ETHYL-1,5-DIMETHYLHEXYLPEROXY ACID ESTERS

BACKGROUND OF THE INVENTION

1. Field of the Invention

This invention relates to novel peracid esters usable as a radical polymerization initiator and a method of producing the same as well as hydroperoxides as a starting material for the peracid ester, and polymerization of vinyl monomer, curing of unsaturated polyester and crosslinking of polymer through the peracid ester.

2. Related Art Statement

In general, it is known to use t-alkyl peracid esters as a polymerization initiator, a curing agent or a crosslinking agent as described in, for example, Japanese Patent Application Publication No. 51-38752 and No. 62-30064, Japanese Patent laid open No. 52-76353 and the like.

In polymer industry, however, it is desired to increase the production of polymer resins without requiring additional construction of expensive production equipments from a viewpoint of economical reasons. Further, it is demanded to develop a more active polymerization initiator for shortening the reaction time and increasing the production volume.

As a polymerization technique, it is known that the polymerization rate can be increased by using the more active polymerization initiator. The production improvement through such a technique is particularly useful in the polymerization of vinyl chloride. Because, in the polymerization of vinyl chloride, the polymerization degree is determined by the polymerization temperature but is not dependent upon the polymerization rate. Therefore, even when the polymerization rate is increased by using the highly active polymerization initiator, if the polymerization temperature is constant, the polymerization degree is unchangeable. That is, the polymerization rate can be enhanced without changing the physical properties of the polymer.

Further, the more active polymerization initiator is desirable to be used for objects other than the above production improvement. That is, such an object is concerned with the production of polyvinyl chlorides having a high polymerization degree.

In general, polyvinyl chlorides having a polymerization degree of not less than 1500 are called as a high polymerization degree product and are known to be particularly excellent in the properties such as mechanical strength, heat stability, dimensional stability, cold resistance and the like.

Furthermore, when flexible polyvinyl chlorides are produced by adding a plasticizer to the polyvinyl chloride, rubbery elasticity can be enhanced as the polymerization degree becomes high.

As shown in the following Table 1, the polymerization degree of the polyvinyl chloride is determined by the polymerization temperature, so that in order to obtain a polyvinyl chloride having a high polymerization degree, vinyl chloride should be polymerized at a relatively low temperature of not higher than 50° C. From this reason, it is desired to develop a polymerization initiator having a sufficient activity even at a low temperature.

TABLE 1

| Polymerization temperature (°C.) | Polymerization degree |
| --- | --- |
| 60 | 800 |
| 57 | 1000 |
| 52 | 1300 |
| 50 | 1500 |
| 45 | 2000 |
| 40 | 2500 |
| 35 | 3000 |

It has hitherto been known to use diisobutyryl peroxide (hereinafter abbreviated as IBPO), acetylcyclohexylsulfonyl peroxide (hereinafter abbreviated as ACSP, Japanese Patent Application Publication No. 40-16795) or the like as a polymerization initiator having an activity even at the low temperature when polymerizing vinyl chloride monomer.

Furthermore, peracid esters such as cumylperoxy neodecanoate (hereinafter abbreviated as CND, Japanese Patent laid open No. 58-120611), t-octylperoxy neodecanoate (hereinafter abbreviated as OND, Japanese Patent laid open No. 58-120613) and the like have been known as a polymerization initiator.

However, there are some problems in the polymerization methods using IBPO, ACSP, CND or OND as a polymerization initiator. That is, IBPO is very unstable against water and is decomposed by contacting with water, so that the polymerization activity is not held and hence the yield of the polymer is low. On the other hand, ACSP has a problem in view of the hygiene of decomposition product and is poor in the heat stability because the resulting polymer is colored. Furthermore, CND produces a peculiar odor in the polymer because of the decomposition product. Moreover, OND hardly affects the properties of the resulting polymer, but is poor in the polymerization activity as compared with ACSP, CND and the like, so that it is small in the effect as a polymerization initiator having an activity at low temperature.

In the field of peroxides, it is well-known that the half-valued period of a certain peroxide (measure on the activity of the peroxide) is remarkably changed by applying various structure variations to the peroxide. For example, in case of an alkyl peracid ester, the activity can be changed by the structure variation of carboxylic group and alkylperoxy group.

The alkyl peracid ester obtained by the conventional technique and having an activity at a lowest temperature is a compound in which the alkylperoxy group is t-octylperoxy group. This compound has an activity at a low temperature as compared with the other peracid ester containing, for example, t-butylperoxy group, t-amylperoxy group, t-hexylperoxy group or the like when the carboxylic group is same.

A temperature requiring that a half-valued period of 1 mol/l of t-butylperoxy neodecanoate, t-amylperoxy neodecanoate or t-hexylperoxy neodecanoate in benzene is 10 hours (hereinafter referred to as 10 hour halflife temperature) is 45°–47° C., while the 10 hour halflife temperature of OND is as low as 41° C. As previously mentioned, however, it is further demanded to develop a polymerization initiator having an activity at a lower temperature in order to conduct low temperature polymerization for the shortening of polymerization time and the increase of production volume.

SUMMARY OF THE INVENTION

The inventors have made various studies over a long time for solving the problems of the conventional techniques and confirmed that a novel compound not reported in an article or 1-ethyl-1,5-dimehtylhexyl peracid ester is short in the half-valued period as compared with the conventional t-alkyl peracid ester having the same carboxylic group and is useful as an initiator having a higher activity, a curing agent or a crosslinking agent. Particularly, it has been found that peracid esters derived from tertiary aliphatic carboxylic acid are very active at low temperature and become a polymerization initiator useful for the polymerization of vinyl chloride monomer, whereby polyvinyl chlorides having a high polymerization degree are obtained in a high yield even at a low temperature of not higher than 50° C. and have excellent heat stability and particularly coloring property and no odor and as a result the invention has been accomplished.

That is, the invention is concerned with 1-ethyl-1,5-dimethylhexyl peroxy acid ester represented by the following general formula (I):

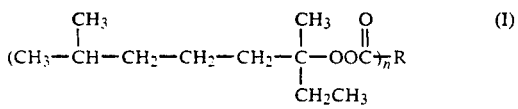

[wherein n is 1 or 2, and when n is 1, R is a cyclohexyl group, a cyclohexenyl group, a phenyl group, a substituted phenyl group,

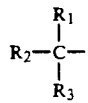

group (in which $R_1$ and $R_2$ are the same or different and represent a hydrogen atom or an alkyl group having a carbon number of 1-8, $R_3$ is a hydrogen atom, an alkyl group having a carbon number of 1-8, an alkoxy group having a carbon number of 1-6, a phenyl group, a substituted phenyl group or a phenoxy group) or

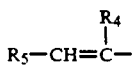

group (in which $R_4$ and $R_5$ are the same or different and represent a hydrogen atom or an alkyl group having a carbon number of 1-4), and when n is 2, R is an alkylene group having a carbon number of 1-10, a cyclohexylene group or a phenylene group] and the use of such a peracid ester for the polymerization and copolymerization of vinyl monomer, the curing of unsaturated polyester resin and the crosslinking of polymers.

And also, the invention is concerned with a method of polymerizing vinyl chloride monomer, in which a particular peracid ester having n=1 and R=tertiary alkyl group having a carbon number of 4-12 in the general formula (I) is used as a polymerization initiator in the polymerization of vinyl chloride monomer or between vinyl chloride monomer and copolymerizable monomer.

DESCRIPTION OF THE PREFERRED EMBODIMENTS

The peracid esters according to the invention have a structure that carbon bonding peroxy group in the t-alkylperoxy group (α-positioned carbon) has a branched methyl, ethyl or isohexyl group, and are novel compounds not reported in the article.

Moreover, the upper limit of the carbon number in $R_1-R_5$ of the general formula (I) is determined by considering the utility. And also, the alkyl or alkylene group may be a straight chain or a branched chain.

A concrete example of the peracid ester according to the invention is as follows:
0 1-ethyl-1,5-dimethylhexyl peroxy neodecanoate;
1-ethyl 1,5-dimethylhexyl peroxy pivalate;
1-ethyl-1,5-dimethylhexyl peroxy-2-ethyl hexanoate;
1-ethyl-1,5-dimethylhexyl peroxy isobutyrate;
1-ethyl-1,5-dimethylhexyl peroxy-3,5,5-trimethyl hexanoate;
1-ethyl-1,5-dimethylhexyl peroxy laurate;
1-ethyl-1,5 dimethylhexyl peroxy acetate;
1-ethyl-1,5-dimethylhexyl peroxy benzoate;
1-ethyl-1,5-dimethylhexyl peroxy phenoxyacetate;
1-ethyl-1,5-dimethylhexyl peroxy acrylate;
di(1-ethyl-1,5-dimethylhexyl peroxy) adipate;
di(1-ethyl-1,5-dimethylhexyl peroxy)-1,4-cyclohexane carboxylate;
di(1-ethyl-1,5-dimethylhexyl peroxy) isophthalate.

The peracid esters according to the invention can be divided into monoperacid ester (n=1) and diperacid ester (n=2). These compounds can be obtained as follows.

That is, an acid halide represented by the following general formula (II):

(wherein n and R are the same as mentioned above, and X is a chlorine atom or a bromine atom) is reacted with 1-ethyl-1,5-dimethylhexyl hydroperoxide in the presence of an alkaline compound and a tertiary amine at a temperature lower than a decomposition temperature of a peroxy acid ester to be produced.

As the alkaline compound useful for the production of the peracid ester according to the invention, mention may be made of NaOH, KOH, LiOH, $Na_2CO_3$ and the like. As the tertiary amine, mention may be made of pyridine, triethylamine, tributylamine and the like.

The peracid ester may be synthesized by using an aromatic hydrocarbon (e.g. toluene, ethylbenzene), an aliphatic hydrocarbon (e.g. hexane, octane, petroleum naphtha, mineral spirit) or an aliphatic hydrocarbon consisting essentially of isoparaffin (e.g. trade name of Shellsol, made by Shell Chemicals, Co., Ltd.) as a solvent, or used by diluting with such a solvent after the synthesis. Moreover, the reaction temperature is not higher than the decomposition temperature of the peracid ester to be synthesized, and is usually about −10° C. −40° C.

The acid chloride to be used in the invention can be obtained by reacting carboxylic acid with a chlorinating agent such as $PCl_3$, $POCl_3$, $SOCl_2$, phosgene or the like and then isolating an acid chloride from the reaction mixture.

As carboxylic acid used in the invention, mention may be made of cyclohexane carboxylic acid, 2-cyclohexene-1-carboxylic acid, benzoic acid, m-methyl benzoic acid, 2,4-dichloro benzoic acid, acetic acid, octanoic acid, lauric acid, 2-ethyl hexanoic acid, 3,5,5-trimethyl hexanoic acid, phenylacetic acid, isobutyric acid, 2-methyl butyric acid, 2-ethyl butyric acid, 2-phenyl butyric acid, 2-methyl valeric acid, pivalic acid, neoheptanoic acid, neooctanoic acid, neononanoic acid, neodecanoic acid (The last four acid are an isomer mixture of carboxylic acids having a total carbon number of 7, 8, 9, 10 among carboxylic acids usually called as "neoacid" in which α-carbon atom of carboxylic acid is completely substituted with an alkyl group. The isomer distribution is disclosed in detail in Japanese Patent Application Publication No. 54-3847), ethoxyacetic acid, phenoxyacetic acid, acrylic acid, methacrylic acid, crotonic acid, 2-methyl crotonic acid and the like.

As dicarboxylic acid, mention may be made of malonic acid, succinic acid, adipic acid, azelaic acid, 1,10-decane dicarboxylic acid, 1,11-undecane dicarboxylic acid, 1,12-dodecane dicarboxylic acid, 1,4-cyclohexane dicarboxylic acid, 1,2-cyclohexane dicarboxylic acid, 4-methyl-1,2-cyclohexane dicarboxylic acid, phthalic acid, isophthalic acid, terephthalic acid and the like.

1-Ethyl-1,5-dimethylhexyl hydroperoxide used in the production of the peracid ester according to the invention is represented by the following structural formula:

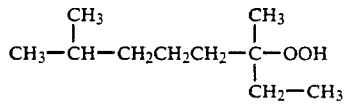

and can be obtained by treating 1-ethyl-1,5-dimethyl hexanol (tetrahydrolinalol) with an excessive amount of hydrogen peroxide in the presence of a strong acid catalyst such as sulfric acid, phosphoric acid, perchloric acid, acid medium of ion exchanger or p-toluene sulfonic acid. Further, the tetrahydrolinalol may be obtained by subjecting a natural linalol or an industrially synthesized linalol to a usual hydrogenation.

The thus synthesized hydroperoxide is also a novel compound. This hydroperoxide is a colorless and transparent liquid, and the chemical structure thereof is determined by identifying confirmation of O—O bond and O—H bond through an infrared absorption spectrum and confirmation of —OOH structure through a nuclear magnetic resonance spectrum. Furthermore, the content of peroxy group can be determined from an active oxygen amount through an iodometry.

The peracid ester according to the invention can be used as a polymerization initiator for vinyl monomers, a curing agent for unsaturated polyester resins or a crosslinking agent for polymers.

The polymerization method when using the peracid ester according to the invention as the polymerization initiator, curing agent or crosslinking agent is as follows.

VINYL POLYERMIZATION

The peracid ester according to the invention is an effective polymerization initiator for polymerization or copolymerization of vinyl monomers.

As the vinyl monomer using the peracid ester according to the invention as a polymerization initiator, mention may be made of olefins such as ethylene, propylene, styrene, α-methylstyrene, chlorostyrene and the like; diolefins such as 1,3-butadiene, isoprene, chloroprene and the like; vinyl esters such as vinyl acetate, vinyl propionate and the like; unsaturated nitriles such as acrylonitrile, methacrylonitrile and the like; acrylic acid, methacrylic acid and esters or amides thereof; halogenated vinyl or vinylidene compounds such as vinyl chloride, vinyl bromide, vinyl fluoride, vinylidene chloride, vinylidene fluoride and the like; perhaloolefines such as ethylene tetrafluoride and the like; vinyl ethers such as methylvinyl ether, butylvinyl ether and the like; and a mixture of the above compounds such as styrene-butadiene, acrylonitrile-butadiene-styrene and the like. The peracid ester according to the invention is preferable to be used in the polymerization of vinyl chloride, styrene, ethylene or methyl methacrylate, particularly suspension polymerization of vinyl chloride monomer.

The amount of the peracid ester added is 0.001-1 part by weight, preferably 0.01-0.5 part by weight as a pure product based on 100 parts by weight of vinyl monomer charged. The polymerization temperature is 20° C.-250° C., preferably 30° C.-200° C.

The peracid ester according to the invention may be used alone or a combination with the other initiator. The latter initiator can properly be selected from the conventionally used initiators in accordance with the polymerization temperature and the like. Furthermore, the amount of such an initiator used can properly be determined in accordance with the desired polymerization temperature, the properties of the resulting polymer and the like.

POLYMERIZATION OF VINYL CHLORIDE

Among the peracid esters according to the invention, peracid esters represented by the following general formula:

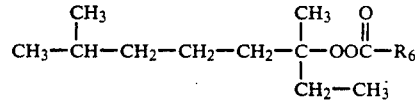

(in which $R_6$ is a tertiary alkyl group having a carbon number of 4–12) are particularly active at a low temperature, and are very useful in the polymerization of vinyl chloride monomer or the polymerization of vinyl chloride monomer with a copolymerizable monomer.

Such a peracid ester concretely includes 1-ethyl-1,5-dimethylhexyl peroxy pivalate, 1-ethyl-1,5-dimethylhexyl peroxy neohexanoate, 1-ethyl-1,5-dimethylhexyl peroxy neononanoate, 1-ethyl-1,5-dimethylhexyl peroxy neodecanoate and the like.

As the other vinyl monomer copolymerizable with vinyl chloride monomer used in the invention, mention may be made of ethylene, vinyl acetate, vinylidene chloride, styrene, acrylic acid ester and the like.

The amount of the peracid ester used may properly be selected, but is usually about 0.001-2 parts by weight, preferably 0.01-1 part by weight as a pure product based on 100 parts by weight of the vinyl chloride monomer charged. When the amount is less than 0.001 part by weight, the polymerization rate becomes slow, while when it exceeds 2 parts by weight, it is difficult to control the polymerization reaction and the properties of the resulting polymer are undesirably degraded.

According to the invention, the particular polymerization initiator may be used alone or a combination with the other polymerization initiator conventionally used.

The other polymerization initiator used in the invention is at least one of peroxyester, diacyl peroxide and peroxy dicarbonate having a 10 hour halflife temperature of 40–65° C.

Concretely, the peroxyester includes tertbutylperoxy pivalate (55° C.), BND (47° C.), OND (41° C.) and the like, and the diacyl peroxide includes 3,5,5-trimethylhexanoyl peroxide (hereinafter abbreviated as NPO, 60° C.), lauroyl peroxide (62° C.), octanoyl peroxide (62° C.) and the like, and the peroxy dicarbonate includes di(2-ethoxyethyl) peroxy dicarbonate (hereinafter abbreviated as OPP, 43° C), di-n-propylperoxy dicarbonate (41° C.), diisopropylperoxy dicarbonate (41° C.) and the like.

The amount of such a polymerization initiator added is properly determined, but is usually $\frac{1}{4}$–4 times of the addition amount of the peracid ester according to the invention.

According to the invention, the polymerization is usually carried out by suspension polymerization method, in which the usual formulation is adopted except the use of the polymerization initiator according to the invention.

The polymerization temperature is generally 10°–75° C., preferably 30–60° C. When the polymerization temperature is lower than 10° C., the polymerization time tends to become long, while when it exceeds 75° C., the life of the polymerization initiator becomes short and it is difficult to obtain a high conversion degree of polymerization. Moreover, in order to obtain a polymer product having a higher polymerization degree, the necessary temperature is merely selected and is not particularly restricted. When the average polymerization degree is 1500, the upper limit of the polymerization temperature is 50° C., but the lower limit thereof is not particularly restricted. However, the lower limit is preferable to be a lowest temperature coolable in a cooling system through the industrially used production method. The preferable polymerization temperature is 20°–50° C.

CURING OF UNSATURATED POLYESTER RESIN

The peracid ester according to the invention is suitable in the curing of the unsaturated polyester resin.

The unsaturated polyester resin using the peracid ester according to the invention as a curing agent usually includes unsaturated polyesters and one or more vinyl monomers.

As the unsaturated polyester, mention may be made of polyesters obtained by esterifying at least one ethylenically unsaturated di- or poly-carboxylic acid or an anhydride or a halide thereof such as maleic acid, fumaric acid, glutaric acid, phthalic acid, itaconic acid, terephthalic acid, tetrahydrophthalic acid or the like with saturated or unsaturated diol or polyol such as ethylene glycol, diethylene glycol, triethylene glycol, 1,2-propane diol, 1,3-propane diol, 1,2-butane diol, 2-butene-1,4-diol, glycerine or the like, and so on.

As the vinyl monomer in the unsaturated polyester resin composition, mention may be made of styrene, vinyl toluene, α-methylstyrene, diallyl phthalate, acrylonitrile, methyl methacrylate and a mixture thereof, which are copolymerizable with the polyester.

The amount of the peracid ester added as a curing agent is usually 0.1–3 parts by weight, preferably 0.5–2 parts by weight based on 100 parts by weight of the unsaturated polyester resin. The curing temperature is about 20–200° C.

CROSSLINKING OF POLYMER

The peracid ester according to the invention is suitable in the crosslinking of the polymer.

As the polymer using the peracid ester as a crosslinking agent, mention may be made of elastomers such as natural rubber, butadiene rubber, isoprene rubber, silicone rubber, ethylene-propylene rubber, ethylene-propylene-ethylidene norbornen rubber, styrenebutadiene rubber and the like; and thermoplastic resins such as polyethylene, polyethylene-vinyl acetate and the like.

The amount of the peracid ester added as a crosslinking agent is usually 0.3–10 parts by weight, preferably 1–5 parts by weight based on 100 parts by weight of the polymer.

The crosslinking reaction is carried out at a temperature of about 100°–200° C. under a pressure of 50–200 kg/cm$^2$.

The aforementioned hydroperoxide as a novel compound can be used as a polymerization initiator for vinyl monomers, a curing agent for unsaturated polyester resins or a crosslinking agent for polymers.

As the vinyl monomer using the hydroperoxide as a polymerization initiator, mention may be made of olefins such as ethylene, propylene, styrene and the like; diolefins such as 1,3-butadiene, isoprene and the like; vinyl esters such as vinyl acetate, vinyl propionate and the like; unsaturated nitriles such as acrylonitrile, methacrylonitrile and the like; acrylic acid, methacrylic acid and esters or amides thereof; halogenated vinyl or vinylidene compounds such as vinyl chloride, vinyl fluoride, vinylidene chloride and the like; perhaloolefins such as ethylene tetrafluoride and the like; vinyl ethers such as methyl vinyl ether and the like; and a mixture of these compounds such as styrene-butadiene, acrylonitrile-butadiene-styrene and the like.

The unsaturated polyester resin using the hydroperoxide as a curing agent usually includes unsaturated polyesters and one or more vinyl monomers.

As the unsaturated polyester, mention may be made of polyesters obtained by esterifying at least one ethylenically unsaturated di- or polycarboxylic acid or an anhydride or a halide thereof such as maleic acid, fumalic acid, glutaric acid, tetrahydrophthalic acid or the like with saturated or unsaturated diol or polyol such as ethylene glycol, diethylene glycol, triethylene glycol, 1,2-propane diol, 1,3-propane diol, 1,2-butane diol, 2-butene-1,4-diol, glycerine or the like.

As the vinyl monomer in the unsaturated polyester resin composition, mention may be made of styrene, vinyl toluene, α-methylstyrene, diallyl phthalate, acrylonitrile, methyl methacrylate and a mixture thereof, which are copolymerizable with the polyester.

As the polymer using the hydroperoxide as a crosslinking agent, mention may be made of polyethylene, ethylene-vinyl acetate copolymer, ethylene-propylene copolymer, ethylene-propylene-diene terpolymer, polybutadiene and the like.

The well-known methods can be utilized to the polymerization, curing and crosslinking using the hydroperoxide according to the invention as they are.

The 1-ethyl-1,5-dimethylhexyl peroxy acid esters according to the invention are novel compounds and have an advantage that the half-reduced time is shorter than that of the conventional t-alkyl peracid esters derived from the same carboxylic acid. Therefore, the polymerization rate can be increased by using as a polymerization initiator the peracid ester according to the invention alone or together with the conventional polymerization initiator. As a result, the polymerization cycle time can be shortened and the production volume can be increased.

Furthermore, the peracid ester according to the invention is high in the activity as a curing agent for the unsaturated polyester resin or a crosslinking agent for the polymer and is useful.

Moreover, the particular peracid esters according to the invention derived from tertiary aliphatic carboxylic acid are particularly active at a low temperature. When these esters are used in the polymerization of the vinyl chloride monomer, the polymerization cycle time can more be shortened and the production volume can be increased. At the same time, the resulting polymer has no odor and coloring and is excellent in the thermal stability.

In addition, the polymerization of vinyl chloride is made possible at a lower temperature by using the particular peracid ester, whereby polyvinyl chloride having more improved properties and a high polymerization degree ca be obtained.

That is, the use of the polymerization initiator according to the invention is excellent in a point that the resulting polymer has a good thermal stability and no odor and coloring as compared with the use of the conventional polymerization initiator (e.g. ACSP, CND). Furthermore, the holdability of polymerization activity is high and the polymerization rate is large as compared with the use of the conventional polymerization initiator (e.g. IBPO, OND). As a result, the invention is excellent in a point that the polymer yield becomes high.

Moreover, 1-ethyl-1,5-dimethylhexyl hydroperoxide used in the production of the above peroxy acid ester is also a novel compound and has peculiar properties owing to its specific structure that carbon bonding the peroxy group (α-positioned carbon) has a branch of methyl group, ethyl group and isohexyl group. Therefore, it is useful as a polymerization initiator for vinyl monomer, a curing agent for unsaturated polyester resin or a crosslinking agent for polymer as well as a starting material for peroxide.

The following examples are given in illustration of the invention and are not intended as limitations thereof.

EXAMPLE 1

Synthesis of 1-ethyl-1,5-dimethylhexyl hydroperoxide

Into a four-necked flask of 300 ml provided with a stirrer was charged a mixed solution of 51.2 g of 50% aqueous solution of hydrogen peroxide and 46.8 g of 8% aqueous solution of sulfuric acid, to which was added dropwise 63.4 g of tetrahydrolinalol at an inner temperature of 10° C. over 10 minutes with stirring. After the addition, the reaction mixture was further stirred at a temperature of 25° C. for 2 hours. The oil phase obtained by separation of the solution was washed with water three times, dried on anhydrous magnesium sulfate, and distilled under vacuum to remove unreacted tetrahydrolinalol, whereby 47.8 g of a colorless and transparent liquid was obtained. The product had an active oxygen amount of 8.72%, a purity of 95.0% and a yield of 65.1 mol%.

The identification of the product was carried out by IR and NMR spectra.

IR spectrum: O—O stretching vibration 858 cm$^{-1}$
OO—H stretching vibration 3370 cm$^{-}$
NMR spectrum (CCl$_4$):

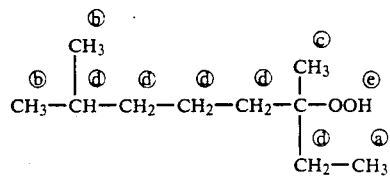

H a :δ0.88, t, 3H
H b :δ0.90, d, 6H
H c :δ1.14, s, 3H
H d :δ1.18-2.10, m, 9H
H e :δ8.02, s, 1H

EXAMPLE 2

Synthesis of 1-ethyl-1,5-dimethylhexyl peroxy neodecanoate

Into a four-necked flask of 200 ml provided with a stirrer was charged 43.4 g of 35% aqueous solution of potassium hydroxide, to which was added 27.5 g of 95.0% 1-ethyl-1,5-dimethylhexyl hydroperoxide synthesized in Example 1 while maintaining a liquid temperature at 15° C. with stirring. Further, 30.5 g of neodecanoic acid chloride was added dropwise at a liquid temperature of 15° C. over 10 minutes with stirring. After the liquid temperature was raised to 20° C. and the stirring was continued for 1 hour, 70 g of cold water was added and further stirred for 5 minutes. The aqueous phase was separated and washed with 100 g of 5% aqueous solution of sodium hydroxide and further with water three times. This solution was dried on anhydrous magnesium sulfate to obtain 40.3 g of a colorless and transparent liquid. This product had an active oxygen amount of 4.42%, a purity of 90.7% and a yield of 74.2 mol%.

The identification of this product was carried out by IR and NMR spectra.

IR spectrum: C=O stretching vibration 1770 cm$^{-1}$
NMR spectrum (CCl$_4$):

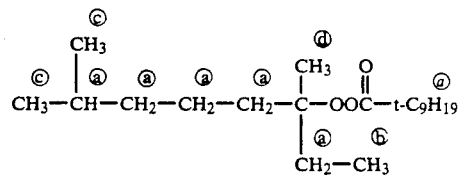

H a :δ0.60-2.20, m, 28H
H b :δ0.88, t, 3H
H c :δ0.90, d, 6H
H d :δ1.20, s, 3H

EXAMPLE 3

Synthesis of other 1-ethyl-1,5-dimethylhexyl peroxy acid ester

The same procedure as in Example 2 was repeated except that a proper amount of another acid chloride was used instead of neodecanoic acid chloride of Example 2 All of the following products were colorless liquids. 1-ethyl-1,5-dimethylhexyl peroxy pivalate (purity: 93.3%, yield: 65.9%)

1-ethyl-1,5-dimethylhexyl peroxy-2-ethyl hexanoate (purity: 95.7%, yield: 61.6%)

1-ethyl-1,5-dimethylhexyl peroxyisobutyrate (purity: 96.1%, yield: 66.2%)

1-ethyl-1,5-dimethylhexyl peroxy laurate (purity: 93.1%, yield: 54.5%)

1-ethyl-1,5-dimethylhexyl peroxy acetate (purity: 94.4%, yield:60.3%)

1-ethyl-1,5-dimethylhexyl peroxy benzoate (purity: 95.8%, yield: 58.8%)

di(1-ethyl-1,5-dimethylhexyl peroxy)-1,4-cyclohexane carboxylate (purity: 94.6%, yield: 64.7%)

EXAMPLE 4

A thermal decomposition test (concentration: 0 1 mol/l) was carried out by using benzene as a solvent. Further, 10 hour halflife temperature ($T_{10}$) was measured with respect to the peracid esters according to the invention synthesized in Examples 2 and 3. For the comparison, the 10 hour halflife temperature was measured with respect to a peracid ester derived from the well-known t-alkyl hydroperoxide. The results are shown in the following table 2.

TABLE 2

| t-alkyl peracid ester | $T_{10}$ (°C.) |
|---|---|
| Peroxy neodecanoate | |
| 1-ethyl-1,5-dimethylhexyl | 40 |
| t-butyl | 47 |
| t-hexyl | 45 |
| t-octyl | 41 |
| Peroxy pivalate | |
| 1-ethyl-1,5-dimethylhexyl | 47 |
| t-butyl | 55 |
| t-octyl | 49 |
| Peroxy-2-ethylhexanoate | |
| 1-ethyl-1,5-dimethylhexyl | 64 |
| t-butyl | 73 |
| t-octyl | 66 |
| Peroxy isobutyrate | |
| 1-ethyl-1,5-dimethylhexyl | 70 |
| t-butyl | 78 |
| t-octyl | 72 |
| Peroxy laurate | |
| 1-ethyl-1,5-dimethylhexyl | 88 |
| t-butyl | 96 |
| t-octyl | 90 |
| Peroxy acetate | |
| 1-ethyl-1,5-dimethylhexyl | 90 |
| t-butyl | 102 |
| t-octyl | 92 |
| Peroxy benzoate | |
| 1-ethyl-1,5-dimethylhexyl | 94 |
| t-butyl | 104 |
| t-octyl | 95 |
| Diperoxy-1,4-cyclohexane carboxylate | |
| di-(1-ethyl-1,5-dimethylhexyl) | 73 |
| di(t-butyl) | 78 |
| di(t-octyl) | 74 |

As seen from Table 2, the 1-ethyl-1,5-dimethylhexyl peroxy acid esters according to the invention are shorter in the half-reduced time than that of the conventional t-alkyl peracid ester derived from the same carboxylic acid.

Polymerization of vinyl chloride

EXAMPLE 5

In a stainless autoclave of 400 ml capacity were placed 200 ml of ion exchanged water and 0.1 part by weight of polyvinyl alcohol. Then, 0.20 mmol of 1-ethyl-1,5-dimethylhexyl peroxy neodecanoate (hereinafter abbreviated as LND) obtained in Example 2 was added, cooled below −80° C. and added with 100 parts by weight of vinyl chloride monomer. A space portion of the autoclave was fully purged with a nitrogen gas and then the autoclave was sealed. Next, the polymerization was carried out by placing the autoclave in a thermostatic chamber held at 45° C. for 8 hours. Moreover, the stirring was carried out by rotating the autoclave in the chamber at 32 rpm. After the polymerization, the reaction product was cooled and the unreacted vinyl chloride monomer was removed therefrom. The resulting white powder was washed with 100 ml of water two times and dried under vacuum. The yield of vinyl chloride polymer was 84% as measured from the weight, and the average polymerization degree was 2020.

In order to examine the thermal stability of the resulting vinyl chloride polymer, the coloring test was carried out as follows, and at the same time the odor was measured. The results are shown in the following Table 3.

(Coloring test)

100 parts by weight of the vinyl chloride polymer, 2.5 parts by weight of dibutyltin maleate and 80 parts by weight of dioctyl phthalate as a plasticizer were mixed and kneaded on a roll at 160° C., which was shaped into a sheet of 1 mm in thickness. The coloring degree of the sheet was observed visually.

EXAMPLES 6 and 7

The polymerization of vinyl chloride was carried out in the same manner as in Example 5 by varying the amount of LND added as a polymerization initiator and the polymerization temperature. The results are also shown in Table 3.

EXAMPLES 8 and 9

The polymerization of vinyl chloride was carried out in the same manner as in Example 5 except that the conventionally used initiator BND or OPP was used in addition to the polymerization initiator LND. The results are also shown in Table 3.

COMPARATIVE EXAMPLES 1-4

The polymerization of vinyl chloride was carried out in the same manner as in Example 5 except that the conventionally used acetylcyclohexyl sulfonyl peroxide (ASCP), diisobutyryl peroxide(IBPO), cumylperoxy neodecanoate (CND), t-octylperoxy neodecanoate (OND) were used as a polymerization initiator. The results are also shown in Table 3.

COMPARATIVE EXAMPLES 5 and 6

The polymerization of vinyl chloride was carried out in the same manner as in Example 5 except that IBPO or OND was added in addition to BND. The results are also shown in Table 3.

TABLE 3

| No. | Initiator | Addition amount of initiator[1] (mmol) | Polymerization temperature (°C.) | Polymer yield[2] (%) | Average polymerization degree | Coloring property | Odor |
| --- | --- | --- | --- | --- | --- | --- | --- |
| Example | | | | | | | |
| 5 | LND | 0.20 | 45 | 84 | 2020 | no coloring | no odor |
| 6 | LND | 0.30 | 40 | 81 | 2510 | no coloring | no odor |
| 7 | LND | 0.40 | 35 | 78 | 3090 | no coloring | no odor |
| 8 | LND | 0.08 | 45 | 83 | 2010 | no coloring | no odor |
|   | BND | 0.08 | | | | | |
| 9 | LND | 0.08 | 45 | 84 | 1990 | no coloring | no odor |
|   | OPP | 0.08 | | | | | |
| Comparative Example | | | | | | | |
| 1 | ACSP | 0.20 | 45 | 83 | 2080 | yellow coloring | no odor |
| 2 | IBPO | 0.20 | 45 | 80 | 2030 | no coloring | no odor |
| 3 | CND | 0.20 | 45 | 84 | 1980 | no coloring | strong odor |
| 4 | OND | 0.20 | 45 | 77 | 2050 | no coloring | no odor |
| 5 | IBPO | 0.08 | 45 | 78 | 2030 | no coloring | no odor |
|   | BND | 0.08 | | | | | |
| 6 | OND | 0.08 | 45 | 75 | 2000 | no coloring | no odor |
|   | BND | 0.08 | | | | | |

Note
[1]value (as pure product) based on 100 parts of vinyl chloride monomer
[2]polymerization time: 8 hours As seen from Table 3, when using the conventional polymerization initiator, the resulting polymers are poor in the heat stability (coloring property) or have an odor, or the yield or the like is low even if the coloring property or odor is good, while according to the invention, these problems are completely solved. Particularly, the absence of odor is favorable in view of operation environment in the shaping working.

Furthermore, it is clear that when the polymerization initiator according to the invention is used together with the conventional polymerization initiator, the polymerization rate can be more increased and consequently the amount of the initiator used can be reduced as compared with the single use.

EXAMPLE 10

The polymerization of vinyl chloride monomer was carried out in the same manner as in Example 5 under the conditions shown in the following Table 4 except that 1-ethyl-1,5-dimethylhexyl peroxy pivalate (hereinafter abbreviated as LPV) was used instead of LND as a polymerization initiator. The results are shown in Table 4.

EXAMPLE 11

The polymerization of vinyl chloride monomer was carried out in the same manner as in Example 5 except that LND was used together with the conventionally used OPP as a polymerization initiator. The results are shown in Table 4.

EXAMPLE 12

The polymerization of vinyl chloride monomer was carried out in the same manner as in Example 5 except that LPV was used as a polymerization initiator and a combination of 90 parts by weight of vinyl chloride and 10 parts by weight of vinyl acetate was used as the vinyl chloride monomer. The results are shown in Table 4.

COMPARATIVE EXAMPLES 7-9

The polymerization of vinyl chloride monomer was carried out in the same manner as in Example 5 under the conditions shown in Table 4 except that the conventionally used t-butylperoxy pivalate (BPV), t-hexylperoxy pivalate (HPV) or t-octylperoxy pivalate (OPV) was used as a polymerization initiator. The results are shown in Table 4.

TABLE 4

| No. | Initiator | Addition amount of initiator[1] (mmol) | Polymerization temperature (°C.) | Polymer yield[2] (%) | Coloring property | Odor |
| --- | --- | --- | --- | --- | --- | --- |
| Example | | | | | | |
| 10 | LPV | 0.20 | 55 | 83 | no coloring | no odor |
| 11 | LPV | 0.08 | 55 | 85 | no coloring | no odor |
|    | OPP | 0.08 | | | | |
| 12 | LND | 0.03[3] | 55 | 79 | no coloring | no odor |
| Comparative Example | | | | | | |
| 7 | BPV | 0.20 | 55 | 70 | no coloring | no odor |
| 8 | HPV | 0.20 | 55 | 77 | no coloring | no odor |
| 9 | OPV | 0.20 | 55 | 81 | no coloring | no odor |

Note
[1]value (as pure product) based on 100 parts of vinyl chloride monomer
[2]polymerization time: 8 hours
[3]value (as pure product) based on a total of 90 parts of vinyl chloride monomer and 10 parts of vinyl acetate monomer As seen from Table 4, the peracid esters according to the invention are high in the polymerization activity and the polymer yield as compared with the conventionally used t-alkyl peracid ester (Polymerization of styrene)

EXAMPLE 12

To a glass ampule of 20 ml capacity was added 10 ml of a sample solution of 0.04 mol of 1-ethyl-1,5-dimethylhexyl peroxy benzoate (polymerization initiator) dissolved in 1 l of styrene, and thereafter air inside the ampule was removed under vacuum and then the ampule was sealed by fusing This ampule was placed in a thermostatic oil chamber at 100° C. to conduct polymerization for 4 hours. Thereafter, the reaction product was taken out from the ampule and the amount of unreacted monomer was quantified by an internal standard method through a gas chromatography to calculate the conversion rate of polymerization. As a result, the conversion rate was 98.8%.

EXAMPLE 13

The bulk polymerization of styrene was carried out in the same manner as in Example 12 except that 1-ethyl-1,5-dimethylhexyl peroxy acetate was used as a polymerization initiator. As a result, the conversion rate was 96.1%.

Polymerization of methyl methacrylate

EXAMPLE 14

To a glass ampule of 20 ml capacity was added 10 ml of a sample solution obtained by addin9 1.5 parts by weight of 1-ethyl-1,5-dimethylhexyl peroxy-2-ethyl hexanoate as a polymerization initiator to 50 parts by weight of methyl methacrylate and 50 parts by weight of benzene, and then air inside the ampule was removed under vacuum and the ampule was sealed by fusing. This ampule was placed in a thermostatic oil chamber at 60° C. to conduct polymerization for 7 hours. Thereafter, the reaction product was taken out from the ampule and then the unreacted monomer was quantified by the internal standard method through gas chromatography to calculate the conversion rate of polymerization. As a result, the conversion rate was 96.2%.

EXAMPLE 15

The solution polymerization of methyl methacrylate was carried out in the same manner as in Example 4 except that 1-ethyl-1,5-dimethylhexyl peroxy isobutyrate was used as a polymerization initiator and the polymerization temperature was 70° C. As a result, the conversion rate was 98.3%.

EXAMPLE 16

The solution polymerization of methyl methacrylate was carried out in the same manner as in Example 14 except that di(1-ethyl-1,5-dimethylhexyl peroxy)-1,4-cyclohexane carboxylate was used as a polymerization initiator and the polymerization temperature was 70° C. As a result, the conversion rate was 95.6%.

Curing of unsaturated polyester resin

EXAMPLE 17

To 100 parts by weight of unsaturated polyester resin (Epolac G-110AL, trade name, made by Nippon Shokubai Kagaku Kogyo K.K.) was added 1 part by weight of 1-ethyl-1,5-dimethylhexyl peroxy laurate as a curing agent, which was then dissolved uniformly. The thus prepared resin was poured into an assembly obtained by inserting a flexible vinyl chloride tube as a frame between two glass plates (160×160×5 mm) and fixing them with a metal fitting member at an interval of 5 mm. This assembly was left to stand in a thermostatic chamber of 100° C. for 30 minutes while positioning the inlet port upward to conduct the curing. After the curing, the mass was cooled to room temperature and taken out from the assembly. Then, the hardness at the surface of the cured product was 51 as measured by means of a Barcol hardness tester.

Crosslinking of ethylene-vinyl acetate copolymer

EXAMPLE 18

To 100 parts by weight of ethylene-vinyl acetate copolymer containing 25% of vinyl acetate were added 1 part by weight of stearic acid and 3 parts by weight of 1-ethyl-1,5-dimethylhexyl peroxy benzoate, which were kneaded in a ball mill at 80°-90° C. and crosslinked in a press at a temperature of 150° C. under a pressure of 150 kg/cm² for 30 minutes.

The following test for chloroform extraction was made with respect to the crosslinked product to measure the gel content. As a result, the gel content was 91.2%.

Test for chloroform extraction

The crosslinked product was cut into about 1 m square and weighed onto a brass net of 100 mesh, and thereafter the net was folded into a bag form so as not to fall out the cut sample therefrom. Then, the extraction was carried out in a Soxhlet extractor for 8 hours, during which chloroform was renewed every 6-8 minutes. After the extraction, the bag was placed in a vacuum dryer and dried until the mass was made constant at 50° C., from which a percentage of the gel content was calculated. The gel content of not less than 90% exhibited that the crosslinking reaction was sufficiently performed.

What is claimed is:

1. 1-ethyl-1,5-dimethylhexyl peroxy acid ester represented by the following formula (I):

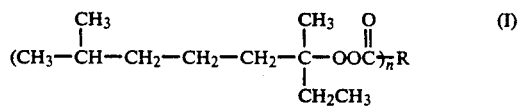

wherein n is 1 or 2, and when n is 1, R is a cyclohexyl group, a cyclohexenyl group, a phenyl group,

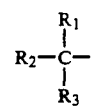

group (in which $R_1$ and $R_2$ are the same or different and represent a hydrogen atom or an alkyl group having a carbon number of 1-8, $R_3$ is a hydrogen atom, an alkyl group having a carbon number of 1-8, an alkoxy group having a carbon number of 1-6, a phenyl group, or a phenoxy group) or

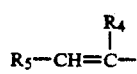

group (in which $R_4$ and $R_5$ are the same or different and represent a hydrogen atom or an alkyl group having a carbon number of 1-4), and when n is 2, R is an alkylene group having a carbon number of 1-10, a cyclohexylene group or a phenylene group.

2. The peracid ester according to claim 1, wherein n is 1 and R is a tertiary alkyl group having a carbon number of 4-12 in said formula (I).

* * * * *